United States Patent
Broka et al.

(10) Patent No.: US 7,074,939 B2
(45) Date of Patent: Jul. 11, 2006

(54) INDOLE DERIVATIVES AS ANTI-INFLAMMATORY AGENTS

(75) Inventors: Chris Allen Broka, Foster City, CA (US); Jeffrey Allen Campbell, Cheshire, CT (US)

(73) Assignee: Roche Palo Alto LLC, Palo Alto, CA (US)

( * ) Notice: Subject to any disclaimer, the term of this patent is extended or adjusted under 35 U.S.C. 154(b) by 0 days.

(21) Appl. No.: 11/065,841

(22) Filed: Feb. 25, 2005

(65) Prior Publication Data

US 2005/0176803 A1 Aug. 11, 2005

Related U.S. Application Data

(62) Division of application No. 10/255,891, filed on Sep. 26, 2002, now Pat. No. 6,872,744.

(60) Provisional application No. 60/325,389, filed on Sep. 27, 2001.

(51) Int. Cl.
 *C07D 209/36* (2006.01)
(52) U.S. Cl. .................................................. 548/484
(58) Field of Classification Search ................ 548/484
 See application file for complete search history.

(56) References Cited

U.S. PATENT DOCUMENTS 4,654,360 A 3/1987 Greenhouse et al.
6,706,662 B1 * 3/2004 Morgenstern et al. ...... 502/345

FOREIGN PATENT DOCUMENTS

| DE | 4338770 A1 | 5/1995 |
|---|---|---|
| EP | 396124 A2 | 11/1990 |
| WO | WO 98/08818 A1 | 3/1998 |
| WO | WO 99/43672 A1 | 9/1999 |

OTHER PUBLICATIONS

"The Canadian Study of Health and Aging: risk factors for Alzheimer's disease in Canada", *Neurology*, (Nov. 1994) 44, 2073-2080.

Ara, G., et al, "Cycloxygenzase and lipoxygenase inhibitors in cancer therapy", *Prostaglindins, Leukotrienes and Essential Fatty Acids*, (1996) No. 54, 3-16.

Breitner, John C.S., et al, "Delayed Onset of Alzheimer's Disease With Nonsteroidal Anti-Inflammatory and Histamine H2 Blocking Drugs", *Neurobiology of Aging*, (1995) 16, No. 4, 523-530.

Eberhart, Charles E., et al, "Up-regulation of Cyclooxygenase 2 Gene Expression in Human Colorectal Adenomas and Adenocarinomas", *Gastroenterology*(1994) No. 107, 1183-1188.

Instel, Paul A., "Analgesic-Antipyretic and Antiinflammatory Agents and Drugs Employed in the Treatment of Gout", *The Pharmaceutical Basis of Therapeutics*, Ninth Edition, McGraw Hill, New York, 196, Chapter 27, 617-657.

Rogers, J., et al, "Clinical trial of indomethacin in Alzheimer's disease", *Neurology*, (1993) 43, 1609-1611.

* cited by examiner

*Primary Examiner*—Kamal A. Saeed
(74) *Attorney, Agent, or Firm*—Grant D. Green

(57) ABSTRACT

This invention relates to compounds, which are generally anti-inflammatory and analgesic compounds, and which are represented by Formula I:

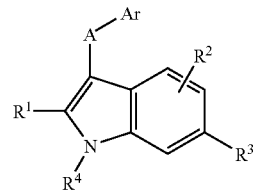

wherein A is a —CH$_2$—, —O—, —S—, or —S(O)—; and the other substituents are as defined in the specification; or individual isomers, mixtures of isomers, and pharmaceutically acceptable salts thereof. The invention further relates to pharmaceutical compositions containing such compounds and methods for their use as therapeutic agents

6 Claims, No Drawings

INDOLE DERIVATIVES AS ANTI-INFLAMMATORY AGENTS

CROSS-REFERENCE

This application is a divisional of U.S. Ser. No. 10/255,891, filed Sep. 26, 2002 now U.S. Pat. No. 6,872,744 which claimed the benefit of priority of U.S. Ser. No. 60/325,389, filed Sep. 27, 2001, both incorporated herein by reference in their entirety.

BACKGROUND OF THE INVENTION

Field of the Invention

This invention relates to anti-inflammatory and analgesic compounds, especially to certain indole derivatives, pharmaceutical compositions containing them, methods for their use, and methods for preparing these compounds.

BACKGROUND OF THE INVENTION

Non-steroidal, anti-inflammatory drugs (NSAIDs), have a problem of causing serious side-effects such as gastrointestinal tract distress or nephro-toxicity. NSAIDs inhibit the activity of cyclooxygenase (COX), which is an enzyme involved in prostaglandin G/H synthesis, resulting in the inhibition of the biosynthesis of prostaglandins not only in inflammatory loci but also in stomach and kidney. It has been found that COX exists in two forms: COX-1 and COX-2, *Cell*, 83, 345, (1995).

COX-1 is expressed in normal cells and controls the function of stomach and kidney, while COX-2 is induced by mitogens or cytokines in inflammatory sites where inflammation and other immunoreactions occur, *J. Biol. Chem.*, 271, 33157(1996).

To avoid the toxicity of NSAIDs due to the inhibition of coexisting COX-1, selective inhibitors of COX-2 have been investigated. The selective COX-2 inhibitors have anti-inflammatory action, pain-relieving action, and/or anti-pyretic action; with less side effects such as bleeding in the gastrointestinal tract. COX-2 inhibitors may show anticancer activity, and lower the induction of asthma in asthmatic patients who are sensitive to conventional NSAIDs. These selective inhibitors of COX-2 may also be used in treating Alzheimer's disease and osteoporosis of women after menopause.

DESCRIPTION OF RELATED ART

U.S. Pat. No. 4,654,360 (assigned to Syntex USA) refers to certain new 3-phenylthioindole derivatives useful as lipoxygenase inhibitors.

EP Patent Application EP396,124 (assigned to Searle) refers to certain new indole-2-carboxylate compounds used for treatment of CNS disorders.

PCT Published Patent Applications WO 98/08818 and WO 99/43672 (assigned to Genetics Inst. Inc.) refers to certain benzimidazolyl-, indolyl-, and quinolyl-benzoic acid derivatives used in the treatment of inflammation disorders.

DE German Application DE 4,338,770 (assigned to Lehr) refers to certain indole derivatives useful as phospholipase A2 inhibitors.

SUMMARY OF THE INVENTION

In a first aspect, this invention provides compounds selected from the group of compounds represented by Formula I:

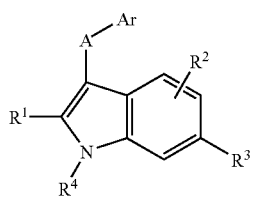

wherein:
A is a —$CH_2$—, —O—, —S—, or —S(O)—;
Ar is an optionally substituted phenyl;
$R^1$ is hydrogen, alkyl, alkoxy, hydroxy, hydroxyalkyl, alkylthio, halo, cyano, —$C(O)NR^5R^6$, —$NR^5R^6$, —$(CR'R'')_{0-3}OC(O)R^5$, —$(CR'R'')_{0-3}SO_2R^5$ and —$(CR'R'')_{0-3}NSO_2R^5$, wherein $R^5$, $R^6$, R', and R'' are each independently in each occurrence hydrogen or alkyl, with the proviso that if A is —$CH_2$—, $R^1$ is not —$C(O)NR^5R^6$;
$R^2$ is hydrogen, alkyl, alkoxy, hydroxy, halo, haloalkyl, nitro, cyano, or —$NR^5R^6$, wherein $R^5$ and $R^6$ are as defined previously;
$R^3$ is —$SOR^7$, —$SO_2R^7$, or —$SO_2NR^5R^6$ wherein $R^7$ is alkyl, hydroxyalkyl, alkoxyalkyl, or alkoxycarbonylalkyl; and $R^5$ and $R^6$ are as defined previously;
$R^4$ is hydrogen or alkyl;
and prodrugs, individual isomers, mixtures of isomers, and pharmaceutically acceptable salts thereof.

In a second aspect, this invention provides pharmaceutical compositions containing a therapeutically effective amount of a compound of Formula I or its pharmaceutically acceptable salt and a pharmaceutically acceptable excipient.

In a third aspect, this invention provides a method of treatment of a disease, in particular an inflammatory or autoimmune disease, in a mammal treatable by administration of a prostaglandin G/H synthase inhibitor, comprising administration of a therapeutically effective amount of a compound of Formula I or its pharmaceutically acceptable salt.

In a fourth aspect, this invention provides processes for preparing compounds of Formula I.

DETAILED DESCRIPTION OF THE INVENTION

Definitions

Unless otherwise stated, the following terms used in the specification and claims have the meanings given below:

"Alkyl" means a linear saturated monovalent hydrocarbon radical of one to six carbon atoms or a branched saturated monovalent hydrocarbon radical of three to six carbon atoms, e.g., methyl, ethyl, n-propyl, 2-propyl, tert-butyl, pentyl, and the like.

"Alkylene" means a linear saturated divalent hydrocarbon radical of one to six carbon atoms or a branched saturated divalent hydrocarbon radical of three to six carbon atoms, e.g., methylene, ethylene, propylene, 2-methylpropylene, pentylene, and the like.

"Alkoxy", "aryloxy", "aralkyloxy", or "heteroaralkyloxy" means a radical —OR where R is an alkyl, aryl, aralkyl, or heteroaralkyl respectively, as defined herein, e.g., methoxy, phenoxy, benzyloxy, pyridin-2-ylmethyloxy, and the like.

"Alkoxycarbonylalkyl" means a radical —$R^a$C(O)$R^b$ where $R^a$ is an alkylene group as defined above and $R^b$ is an alkoxy group as defined above e.g., methoxycarbonylethyl, ethoxycarbonylbutyl, and the like.

"Alkylthio" means the radical —SR, wherein R is a lower alkyl radical as defined herein. Examples of alkylthio radicals include, but are not limited to, methylthio, butylthio, and the like.

"Aryl" means a monovalent monocyclic or bicyclic aromatic radical of 6 to 10 ring atoms which is substituted independently with one to five substituents, preferably one, two, or three substituents selected from alkyl, cycloalkyl, cycloalkylalkyl, halo, nitro, cyano, hydroxy, alkoxy, amino, acylamino, alkylamino, dialkylamino, haloalkyl, haloalkoxy, heteroalkyl, —COR (where R is hydrogen, alkyl, cycloalkyl, phenyl or phenylalkyl), —(CR'R")$_n$COOR (where n is an integer from 0 to 5, R' and R" are independently hydrogen or alkyl, and R is hydrogen, alkyl, cycloalkyl, cycloalkylalkyl, phenyl or phenylalkyl) or —(CR'R")$_n$CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl). More specifically the term aryl includes, but is not limited to, phenyl, biphenyl, 1-naphthyl, and 2-naphthyl, and the derivatives thereof.

"Halogen" or "halo" means the radical fluoro, bromo, chloro, and/or iodo.

"Haloalkyl" means alkyl substituted with one or more same or different halo atoms, e.g., —$CH_2Cl$, —$CF_3$, —$CH_2CF_3$, —$CH_2CCl_3$, and the like, and further includes those alkyl groups such as perfluoroalkyl in which all hydrogen atoms are replaced by fluorine atoms.

"Hydroxyalkyl" means an alkyl radical as defined herein, substituted with one or more, preferably one, two or three hydroxy groups, provided that the same carbon atom does not carry more than one hydroxy group. Representative examples include, but are not limited to, 2-hydroxyethyl, 2-hydroxypropyl, 3-hydroxypropyl, 1-hydroxymethyl-2-methylpropyl, 2-hydroxybutyl, 3-hydroxybutyl, 4-hydroxybutyl, 2,3-dihydroxypropyl, 1-hydroxymethyl-2-hydroxyethyl, 2,3-dihydroxybutyl, 3,4-dihydroxybutyl and 2-hydroxymethyl-3-hydroxypropyl, preferably 2-hydroxyethyl, 2,3-dihydroxypropyl and 1-hydroxymethyl-2-hydroxyethyl. Accordingly, as used herein, the term "hydroxyalkyl" is used to define a subset of heteroalkyl groups.

"Optionally substituted phenyl" means a phenyl ring which is optionally substituted independently with one to four substituents, preferably one or two substituents selected from alkyl, cycloalkyl, cycloalkylalkyl, halo, nitro, cyano, hydroxy, alkoxy, amino, acylamino, monoalkylamino, dialkylamino, haloalkyl, haloalkoxy, heteroalkyl, —COR (where R is hydrogen, alkyl, phenyl or phenylalkyl, —(CR'R"), —COOR (where n is an integer from 0 to 5, R' and R" are independently hydrogen or alkyl, and R is hydrogen, alkyl, cycloalkyl, cycloalkylalkyl, phenyl or phenylalkyl), or —(CR'R")$_n$CONR$^a$R$^b$ (where n is an integer from 0 to 5, R' and R" are independently hydrogen or alkyl, and R$^a$ and R$^b$ are, independently of each other, hydrogen, alkyl, cycloalkyl, cycloalkylalkyl, phenyl or phenylalkyl).

"Leaving group" has the meaning conventionally associated with it in synthetic organic chemistry i.e., an atom or group capable of being displaced by a nucleophile and includes halo (such as chloro, bromo, iodo), alkanesulfonyloxy, arenesulfonyloxy, alkylcarbonyloxy (e.g. acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

"Pharmaceutically acceptable salt" of a compound means a salt that is pharmaceutically acceptable and that possesses the desired pharmacological activity of the parent compound. Such salts include:

(1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1-carboxylic acid, glucoheptonic acid, 3-phenylpropionic acid, trimethylacetic acid, t-butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Prodrugs" means any compound which releases an active parent drug, or any compound which changes its oxidation level, according to Formula I in vivo when such prodrug is administered to a mammalian subject. Prodrugs of a compound of Formula I are prepared by modifying functional groups present in the compound of Formula I in such a way that the modifications may be cleaved in vivo to release the parent compound. Prodrugs may also be prepared by incomplete oxidation of certain functional groups such as sulfur containing groups, in such a way that the oxidation of said functional groups may be effected in vivo to release a compound according to Formula I. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to esters (e.g., acetate, formate, and benzoate derivatives) or carbamates (e.g., N,N-dimethylaminocarbonyl) of hydroxy functional groups, and thiol or sulfoxide groups in compounds of Formula I, and the like.

"Protecting group" refers to a grouping of atoms that when attached to a reactive group in a molecule masks, reduces or prevents that reactivity. Examples of protecting groups can be found in T. W. Greene and P. G. Futs, *Protective Groups in Organic Chemistry*, (Wiley, 2nd ed. 1991) and Harrison and Harrison et al., *Compendium of Synthetic Organic Methods*, Vols. 1–8 (John Wiley and Sons. 1971–1996). Representative amino protecting groups include formyl, acetyl, trifluoroacetyl, benzyl, benzyloxycarbonyl (CBZ), tert-butoxycarbonyl (Boc), trimethylsilyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers, and allyl ethers.

"Treating" or "Treatment" of a Disease Includes:

(1) preventing the disease, i.e., causing the clinical symptoms of the disease not to develop in a mammal that may be exposed to or predisposed to the disease but does not yet experience or display symptoms of the disease, (2) inhibiting the disease, i.e., arresting or reducing the development of the disease or its clinical symptoms, or (3) relieving the disease, i.e., causing regression of the disease or its clinical symptoms.

"A therapeutically effective amount" means the amount of a compound that, when administered to a mammal for treating a disease, is sufficient to effect such treatment for the disease. The "therapeutically effective amount" will vary depending on the compound, the disease and its severity, and the age, weight, etc., of the mammal to be treated.

"Optional" or "optionally" in the above definitions means that the subsequently described event or circumstance may but need not occur, and that the description includes instances where the event or circumstance occurs and instances in which it does not. For example, "heterocyclo group optionally mono- or di-substituted with an alkyl group" means that the alkyl may but need not be present, and the description includes situations where the heterocyclo group is mono- or di-substituted with the alkyl group and situations where the heterocyclo group is not substituted with the alkyl group.

Compounds that have the same molecular formula but differ in the nature or sequence of bonding of their atoms or the arrangement of their atoms in space are termed "isomers". Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn, Ingold and Prelog, (Cahn et al. *Angew. Chem. Inter. Edit.*, 5, 385; (1966) errata 511; Cahn et al. *Angew. Chem.*, 78, 413; (1966) Cahn and Ingold *J. Chem. Soc.* (London), 612; (1951) Cahn et al. *Experientia*, 12, 81; (1956), Cahn, *J. Chem. Educ.*, 41, 116, (1964)) or by the manner in which the molecule rotates the plane of polarized light and designated as dextrorotatory or levoro tatory (i.e., as (+) or (−)-isomers respectively). A chiral compound can exist as either individual enantiomer or as a mixture thereof. A mixture containing equal proportions of the enantiomers is called a "racemic mixture".

The compounds of this invention may exist in stereoisomeric form if they possess one or more asymmetric centers or a double bond with asymmetric substitution and, therefore, can be produced as individual stereoisomers or as mixtures. Unless otherwise indicated, the description is intended to include individual stereoisomers as well as mixtures. The methods for the determination of stereochemistry and the separation of stereoisomers are well-known in the art (see discussion in Chapter 4 of "Advanced Organic Chemistry", 4th edition J. March, John Wiley and Sons, New York, 1992).

Throughout the application the following abbreviations are used with the following meanings:

DMF N,N-Dimethylformamide
DMSO Dimethylsulfoxide
EtOAc Ethyl Acetate
HMPA Hexamethylphosphoric triamide
HPLC High pressure liquid chromatography
KHMDS Potassium hexamethyldisilazide
MCPBA m-Chloroperbenzoic acid
MHz Megahertz
MS Mass Spectrum
NMR Nuclear Magnetic Resonance
OXONE™ Potassium peroxymonosulfate
PCC Pyridinium chlorochromate
PIFA Bis(trifluoroacetoxy)iodobenzene
p-TsOH p-Toluenesulfonic acid
TFAA Trifluoroacetic anhydride
TFA Trifluoroacetic acid
THF Tetrahydrofuran
TLC Thin layer chromatography
TMS-OTf Trimethylsilyl trifluoromethanesulfonate
(BOC)$_2$O Di-tert-butyl dicarbonate Nomenclature The naming and numbering of the compounds of this invention is illustrated below.

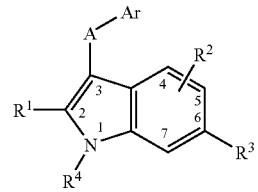

Formula I

In general, the nomenclature used in this Application is based on AUTONOM™ v.4.0, a Beilstein Institute computerized system for the generation of IUPAC systematic nomenclature.

Representative Compounds of This Invention are as Follows:

Compounds of Formula I wherein $R^1$, $R^2$, $R^3$, $R^4$, A, and Ar are as defined below:

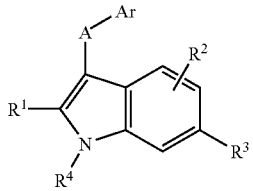

Formula I

| Cpd # | R¹ | R² | R⁴ | R³ | A | Ar | MS. [m + H]⁺ |
|---|---|---|---|---|---|---|---|
| 202 | —CH₃ | H | H | CH₂SO₂— | —CH₂— | 4-fluoro-phenyl | 318 |
| 401 | —CH₃ | H | H | CH₃SO₂— | —O— | 4-fluoro-phenyl | 320 |
| 101 | —CH₃ | H | H | CH₃SO₂— | —S— | 4-fluoro-phenyl | 336 |
| 212 | —CH₃ | H | H | CH₃SO₂— | —CH₂— | 4-chloro-phenyl | 335 |
| 201 | —CH₃ | H | H | CH₃SO₂— | —CH₂— | 4-bromo-phenyl | 379 |
| 106 | —CH₃ | H | H | CH₃SO₂— | —SO— | 4-fluoro-phenyl | 352 |
| 203 | —CH₃ | H | H | CH₃SO₂— | —CH₂— | 3-fluoro-phenyl | 318 |
| 102 | —CH₃ | H | H | CH₃SO₂— | —S— | 4-methoxy-phenyl | 348 |
| 103 | —CH₃ | H | H | CH₃SO₂— | —S— | 4-chloro-phenyl | 353 |
| 204 | —CH₃ | H | H | CH₃SO₂— | —CH₂— | 4-methoxy-phenyl | 318 |
| 205 | —CH₃ | H | H | CH₃SO₂— | —CH₂— | naphthalen-2-yl | 350 |
| 402 | —CH₃ | H | H | CH₃SO₂— | —O— | 2-chloro-4-methoxy-phenyl | 367 |
| 403 | —CH₃ | H | H | CH₃SO₂— | —O— | 2,4-difluoro-phenyl | 338 |
| 404 | —CH₃ | H | H | CH₃SO₂— | —O— | 2,4-dichloro-phenyl | 371 |
| 405 | —CH₃ | H | H | CH₃SO₂— | —O— | 4-chloro-phenyl | 337 |
| 206 | —CH₃ | H | H | CH₃SO₂— | —CH₂— | 4-methyl-phenyl | 314 |
| 207 | —CH₃ | H | H | CH₃SO₂— | —CH₂— | 4-trifluoromethyl-phenyl | 368 |
| 208 | —CH₃ | H | H | CH₃SO₂— | —CH₂— | 2,4-difluoro-phenyl | 336 |
| 209 | —CH₃ | H | H | CH₃SO₂— | —CH₂— | 4-methylsulfanyl-phenyl | 346 |
| 210 | —CH₃ | H | H | CH₃SO₂— | —CH₂— | 4-methoxy-naphthalen-1-yl | 380 |
| 211 | —CH₃ | H | H | CH₃SO₂— | —CH₂— | 2-chloro-phenyl | 335 |
| 104 | —CH₃ | H | H | CH₃SO₂— | —S— | 2,4-difluoro-phenyl | 354 |
| 105 | —CH₃ | H | H | CH₃SO₂— | —S— | 2-chloro-4-fluoro-phenyl | 371 |
| 213 | —CH₃ | H | H | CH₃SO₂— | —CH₂— | 4-methanesulfonyl-phenyl | 378 |
| 502 | —CH₂OH | H | H | CH₃SO₂— | —S— | 4-fluoro-phenyl | 352 |
| 302 | —CN | H | H | CH₃SO₂— | —S— | 4-fluoro-phenyl | 347 |
| 301 | —CN | H | H | CH₃SO₂— | —S— | 2,4-difluoro-phenyl | 365 |
| 303 | —CN | H | H | CH₃SO₂— | —S— | 4-methyl-phenyl | 343 |
| 304 | —CN | H | H | CH₃SO₂— | —S— | 4-methoxy-phenyl | 359 |
| 305 | —CN | H | H | CH₃SO₂— | —S— | 2-chloro-phenyl | 364 |
| 306 | —CN | H | H | CH₃SO₂— | —S— | 2-chloro-4-methoxy-phenyl | 394 |
| 319 | —CONH₂ | H | H | CH₃SO₂— | —S— | 4-fluoro-phenyl | 365 |
| 318 | —CONH₂ | H | H | CH₃SO₂— | —S— | 2,4-difluoro-phenyl | 383 |
| 320 | —CONH₂ | H | H | CH₃SO₂— | —S— | 4-methyl-phenyl | 361 |
| 317 | —CONH₂ | H | H | CH₃SO₂— | —S— | 4-methoxy-phenyl | 377 |
| 315 | —CONH₂ | H | H | CH₃SO₂— | —S— | 2-chloro-4-methoxy-phenyl | 412 |
| 316 | —CONH₂ | H | H | CH₃SO₂— | —S— | 2-chloro-phenyl | 382 |
| 307 | —CN | H | H | CH₃SO₂— | —S— | 4-chloro-phhenyl | 364 |
| 308 | —CN | H | H | CH₃SO₂— | —S— | 2-fluoro-4-methoxy-phenyl | 377 |
| 309 | —CN | H | H | CH₃SO₂— | —SO— | 2,4-difluoro-phenyl | 381 |
| 501 | —CH₂OH | H | H | CH₃SO₂— | —S— | phenyl | 334 |
| 601 | —CH₂SO₂CH₃ | H | H | CH₃SO₂— | —S— | 2-chloro-phenyl | 431 |
| 801 | —C(O)H | H | H | CH₃SO₂— | —S— | 2-chloro-phenyl | 366 |
| 701 | —CH₂OC(O)CH₃ | H | H | CH₃SO₂— | —S— | 2-chloro-phenyl | 411 |
| 321 | —CON-nBu | H | H | CH₃SO₂— | —S— | 2,4-difluoro-phenyl | 439 |
| 322 | —CON-iPr | H | H | CH₃SO₂— | —S— | 2,4-difluoro-phenyl | 425 |
| 327 | —CONEt | H | H | CH₃SO₂— | —S— | 2,4-difluoro-phenyl | 411 |
| 323 | —CON(Me)₂ | H | H | CH₃SO₂— | —S— | 2,4-difluoro-phenyl | 411 |
| 324 | —CON(Et)₂ | H | H | CH₃SO₂— | —S— | 2,4-difluoro-phenyl | 439 |
| 325 | —CON-nPr | H | H | CH₃SO₂— | —S— | 2,4-difluoro-phenyl | 425 |
| 326 | —CONMe | H | H | CH₃SO₂— | —S— | 2,4-difluoro-phenyl | 397 |
| 311 | —CN | H | H | CH₃SO₂— | —S— | 4-ethoxy-phenyl | 373 |
| 328 | —CON-iPr | H | H | CH₃SO₂— | —S— | 2-fluoro-phenyl | 366 |
| 329 | —CON-nBu | H | H | CH₃SO₂— | —S— | 2-fluoro-phenyl | 420 |
| 330 | —CONEt | H | H | CH₃SO₂— | —S— | 2-fluoro-phenyl | 393 |

-continued

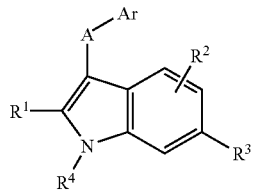

Formula I

| Cpd # | R¹ | R² | R⁴ | R³ | A | Ar | MS. [m + H]⁺ |
|---|---|---|---|---|---|---|---|
| 331 | —CON-nPr | H | H | $CH_3SO_2$— | —S— | 2-fluoro-phenyl | 407 |
| 332 | —CON-iPr | H | H | $CH_3SO_2$— | —S— | 2-chloro-phenyl | 407 |
| 333 | —CON-nBu | H | H | $CH_3SO_2$— | —S— | 2-chloro-phenyl | 438 |
| 334 | —CONEt | H | H | $CH_3SO_2$— | —S— | 2-chloro-phenyl | 410 |
| 335 | —CON(Et)₂ | H | H | $CH_3SO_2$— | —S— | 2-chloro-phenyl | 438 |
| 336 | —CONMe | H | H | $CH_3SO_2$— | —S— | 2-fluoro-phenyl | 379 |
| 337 | —CON(Me)₂ | H | H | $CH_3SO_2$— | —S— | 2-fluoro-phenyl | 393 |
| 338 | —CON(Et)₂ | H | H | $CH_3SO_2$— | —S— | 2-fluoro-phenyl | 421 |

PREFERRED EMBODIMENTS

While the broadest definition of this invention is set forth in the Summary of the invention, certain compounds of Formula I are preferred.

In certain preferred embodiments Ar is a phenyl optionally substituted at one or more positions, preferably by one to two substitutents independently selected from the group consisting of halo and alkoxy, and R³ is —SO₂R⁶, wherein R⁶ is alkyl.

Within the foregoing preferred embodiment, another preferred group of compounds is that wherein Ar is phenyl optionally substituted at one or more positions, preferably by one to two substitutents independently selected from the group consisting of halo and alkoxy; R³ is —SO₂R⁶, wherein R⁶ is alkyl; A is —O—; and yet a more preferred group of compounds is that wherein Ar is phenyl optionally substituted at one or more positions, preferably by one to two substitutents independently selected from the group consisting of halo and alkoxy; R³ is —SO₂R⁶, wherein R⁶ is alkyl; A is —O—; and R¹ is alkyl or cyano.

In another preferred embodiment a preferred group of compounds is that wherein Ar is phenyl optionally substituted at one or more positions, preferably by one to two substitutents independently selected from the group consisting of halo and alkoxy; R³ is —SO₂R⁶; wherein R⁶ is alkyl; and A is —S—; and yet a more preferred group of compounds is that wherein Ar is phenyl optionally substituted at one or more positions, preferably by one to two substitutents independently selected from the group consisting of halo and alkoxy; R³ is —SO₂R⁶, wherein R⁶ is alkyl; A is —S—; and R¹ is alkyl or cyano.

In another preferred embodiment a preferred group of compounds is that wherein Ar is phenyl optionally substituted at one or more positions, preferably by one to two substitutents independently selected from the group consisting of halo and alkoxy; R³ is —SO₂R⁶, wherein R⁶ is alkyl; and A is —CH₂—; and yet a more preferred group of compounds is that wherein Ar is phenyl optionally substituted at one or more positions, preferably by one to two substitutents independently selected from the group consisting of halo and alkoxy; R³ is —SO₂R⁶, wherein R⁶ is alkyl; A is —CH₂—; and R¹ is alkyl or cyano.

While the broadest definition of the invention is set forth in the Summary of the Invention, certain compounds of Formula I are preferred. For example, preferred compounds of Formula I are those in which R¹ is cyano or alkyl, R² is hydrogen or alkyl, R³ is alkylsulfonyl, A is —S— or —O—, and Ar is unsubstituted, monosubstituted, or disubstituted phenyl. Even more preferred compounds of Formula I are those in which A is —S— or —O—, R¹ is cyano, R² is hydrogen, R³ is alkylsulfonyl, and Ar is a phenyl mono or disubstituted with halo or alkoxy.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as *Fieser and Fieser's Reagents for Organic Synthesis*, Volumes 1–17 (John Wiley and Sons, 1991); *Rodd's Chemistry of Carbon Compounds*, Volumes 1–5 and Supplementals (Elsevier Science Publishers, 1989); *Organic Reactions*, Volumes 1–40 (John Wiley and Sons, 1991); *March's Advanced Organic Chemistry*, (John Wiley and Sons, 4ᵗʰ Edition); and *Larock's Comprehensive Organic Transformations* (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography, and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

A person of ordinary skill in the art will have no difficulty, having regard to that skill and this disclosure, in determining how to synthesize compounds of this invention.

Preparation of Compounds of Formula I

Schemes A, B, and C, describe methods to prepare the compounds of Formula I.

Scheme A

Scheme A describes the synthesis of a compound of Formula I wherein A is —S— or —CH$_2$—; R$^1$ is methyl; R$^4$ is hydrogen; R$^3$ is RS(O)$_{1-2}$ (R is alkyl); and R$^2$ and Ar are as defined in the Summary of the Invention.

for the reaction are alcohols (such as methanol and ethanol) or halogenated solvents (such as dichloromethane, chloroform, and the like). The sulfoxides of Formula (4) may be similarly converted to the corresponding sulfones. It is appreciated that this second oxidation may be performed at various points in Scheme A as may be required by the skilled artisan.

In Step 4, a certain sulfonylindole of Formula (4), wherein R is alkyl, preferably wherein R is methyl, can be coupled with a thiophenol of general formula ArSH by stirring in a suitable solvent, such as hexafluoroisopropanol, in the presence of PIFA to provide the compound of Formula (I) wherein A is —S—; or it can be treated with a benzaldehyde of general formula ArCHO in the presence of TMS-OTf in

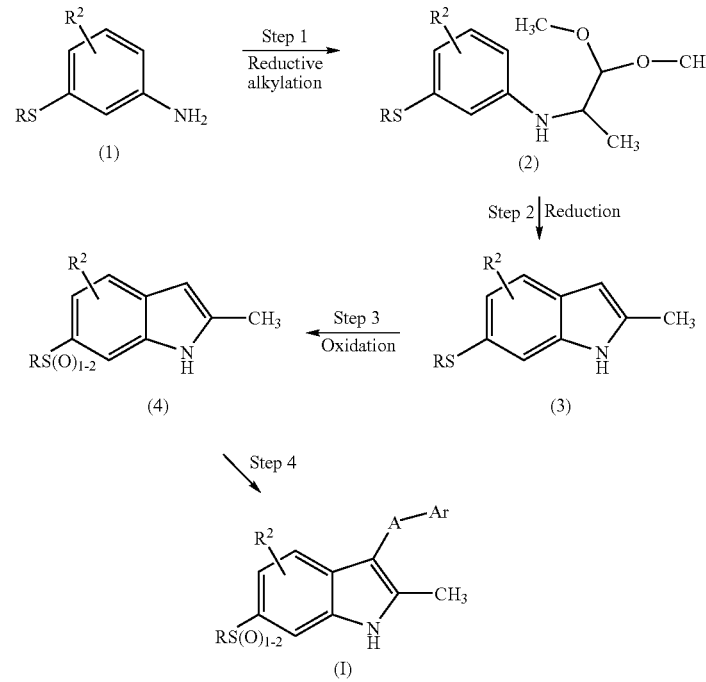

In Step 1, a certain alkylthioaniline of Formula (1), wherein R is alkyl, preferably wherein R is methyl, can undergo a reductive alkylation to give certain compounds of Formula (2). In general, the compounds of Formula (1) are commercially available or can be readily synthesized by those of ordinary skill in the art. For example, 3-methylsulfanyl-aniline can be prepared following the procedures described in Goldkamp, A. H.; *J. Org. Chem.*, 34, 6; (1969), 1780–1785.

In Step 2, a certain indole of Formula (3) wherein R is alkyl, preferably wherein R is methyl, can be prepared by methods known in the art. For example, 2-alkyl-6-alkylthioindoles can be prepared under reductive conditions following the procedures described in Allais, A., et al., *Eur. J. Med. Chem.—Chim. Ther.* 10(2) 187–99 (1975).

In Step 3, the —SR group of a certain compound of Formula (3) wherein R is alkyl, preferably wherein R is methyl, can be oxidized with MCPBA, OXONE™, and the like, to provide a sulfoxide or a sulfone of Formula (4), wherein R is alkyl, preferably R is methyl. Suitable solvents a suitable solvent, such as dichloromethane, followed by treatment with triethylsilane to provide the compound of Formula (I) wherein A is —CH$_2$—.

Scheme B

Scheme B describes the synthesis of a compound of Formula I wherein A is —O—, and R$^1$, R$^2$, R$^3$ and Ar are as defined in the Summary of the Invention.

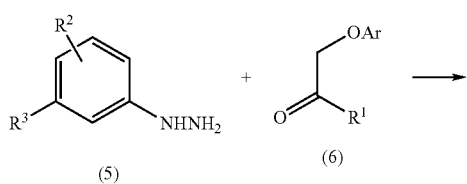

-continued

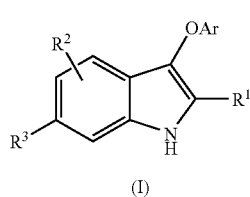

(I)

An indole of Formula (I) may be synthesized from certain compounds of Formula (5) and Formula (6) by methods known in the art. For example 2,3-diphenyl-1H-indole can be prepared following the procedures described in Baccolin, G.; et al.; *J Chem Soc, Chem Commun*, 1981, 11, 563.

Scheme C

Scheme C describes the synthesis of a compound of Formula I wherein A is —S— or CH$_2$, R$^1$ is —CN or —C(O)NR$^4$R$^5$, R$^3$ is RS(O)$_{1-2}$ (R is alkyl), and R$^2$ and Ar are as defined in the Summary of the Invention.

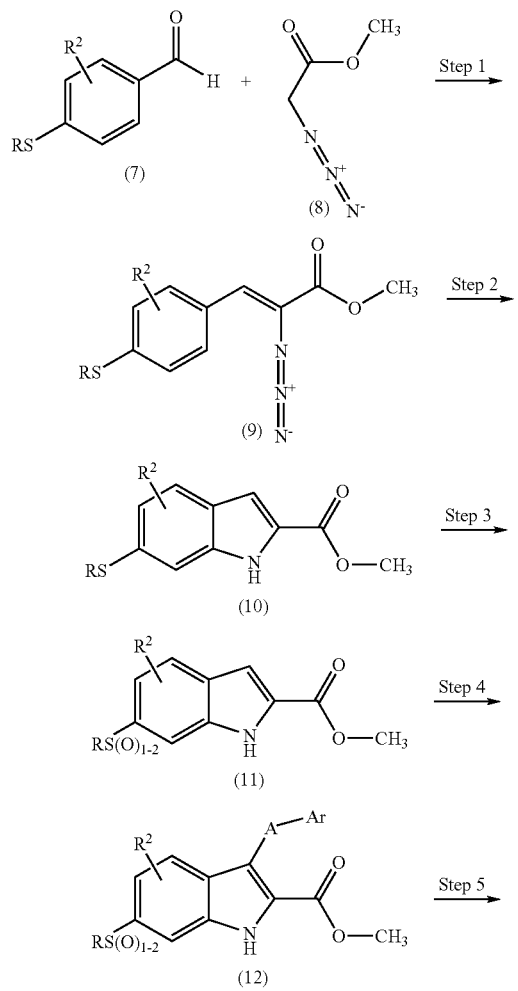

-continued

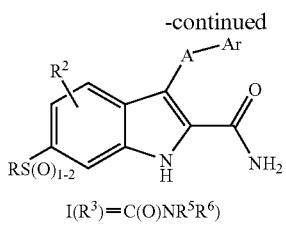

I(R$^3$)=C(O)NR$^5$R$^6$)

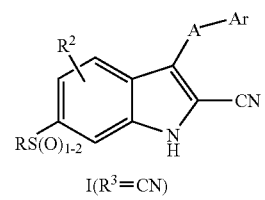

I(R$^3$=CN)

In Step 1, a certain alkylthiobenzaldehyde, of Formula (7), can undergo a condensation with an azido-acetic acid ester of Formula (8), to form a certain compound of Formula (9). In general, the compounds of Formula (7) are commercially available or can be readily synthesized by those of ordinary skill in the art. For example, 4-mercapto-benzaldehyde can be prepared following the procedures described in Arnould, J. C.; et al.; *Tetrahedron Lett.*, 1996, 37(26), 4523–4524. In general the compounds of Formula (8) are commercially available or can be readily synthesized by those of ordinary skill in the art. For example 2-azido-propionic acid ethyl ester can be prepared by following the procedures described in Thomas, A. S.; et al.; *J Org Chem*, 1993, 58(22), 5886–5888.

In Step 2, an indole of Formula (10) can be prepared from a certain compound of Formula (9) by methods known in the art. For example 7-Bromo-4-methoxy-1H-indole-2-carboxylic acid methyl ester can be prepared following the procedures described in Semerth, S.; et al.; *J. Heterocycl. Chem.*, 1981, 18, 1373–1377.

In Step 3, the —SR group of a certain compound of Formula (10) wherein R is alkyl, preferably wherein R is methyl, can be oxidized with MCPBA, OXONE™, and the like to provide a sulfoxide or a sulfone of Formula (11), wherein R is alkyl, preferably R is methyl. Suitable solvents for the reaction are alcohols (such as methanol and ethanol) or halogenated solvents (such as dichloromethane, chloroform, and the like). Sulfoxides of Formula (11) may be similarly converted to the corresponding sulfones. It is appreciated that this second oxidation may be performed at various points in Scheme C as may be required by the skilled artisan.

In Step 4, a certain sulfonylindole of Formula (11), wherein R is alkyl, preferably wherein R is methyl, can be coupled with a thiophenol of general formula ArSH by stirring in a suitable solvent, such as hexafluoroisopropanol, in the presence of PIFA to provide the compound of Formula (12) wherein A is —S—; or it can be treated with a benzaldehyde of general formula ArCHO in the presence of TMS-OTf in a suitable solvent, such as dichloromethane, followed by treatment with triethylsilane to provide the compound of Formula (12) wherein A is —CH$_2$—.

In Step 5, a certain carboxylic acid of Formula (12) can undergo an amidation to give a certain compound of Formula (I). The above amidation can be performed by methods known in the art.

In Step 6, a certain amid of Formula (I) can be converted to a certain indolenitrile of Formula (I) by methods known in the art.

General Utility

The compounds of the invention are inhibitors of prostaglandin G/H Synthase I and II (COX I and COX II), especially COX II, in vitro, and as such are expected to possess both anti-inflammatory and analgesic properties in vivo. See, for example, Goodman and Gilmans's "The Pharmacological Basis of Therapeutics", Ninth Edition, McGraw Hill, N.Y., 1996, Chapter 27. The compounds, and compositions containing them, are therefore useful as anti-inflammatory and analgesic agents in mammals, especially humans. They find utility in the treatment of fever, inflammation, and pain caused by conditions such as rheumatic fever, symptoms associated with influenza or other viral infections, low back and neck pain, dysmenorrhoea, headache, dental pain, sprains, strains, sports injuries, bursitis, tendonitis, myositis, synovitis, arthritis (rheumatoid arthritis and osteoarthritis), gout, ankylosing spondylitis, burns, or injuries. They maybe used to inhibit prostanoid-induced smooth muscle contractions (e.g., in the treatment of dysmenorrhoea, premature labor, and asthma) and to treat autoimmune disorders (such as systemic lupus erythematosus and type I diabetes).

As inhibitors of prostaglandin G/H Synthase, the compounds of this invention are also expected to be useful in the prevention and treatment of cancer, in particular colon cancer. It has been shown that COX-2 gene expression is upregulated in human colorectal cancers and that drugs that inhibit prostaglandin G/H Synthase are effective in animal models of cancer (Eberhart, C. E., et. al., *Gastroenterology*, 107, 1183–1188, (1994); and Ara, G. and Teicher, B. A., *Prostaglandins, Leukotrienes and Essential Fatty Acids*, 54, 3–16, (1996)). In addition, there is epidemiological evidence that shows a correlation between use of drugs that inhibit prostaglandin G/H synthase and a reduced risk of developing colorectal cancer, (Heath, C. W. Jr., et. al., *Cancer*, 74, No. 10, 2885–8, (1994)).

The compounds of this invention are also expected to be useful in the prevention and treatment of Alzheimer's disease. Indomethacin, an inhibitor of prostaglandin G/H synthase, has been shown to inhibit the cognitive decline of Alzheimer's patients, (Rogers, J., et. al., *Neurology*, 43, 1609, (1993)). Also, the use of drugs which inhibit prostaglandin G/H synthase has been linked epidemiologically with a delayed onset of Alzheimer's disease, (Breitner, J. C. S., et. al., *Neurobiology of Aging*, 16, No. 4, 523, (1995) and *Neurology*, 44, 2073, (1994)).

Testing

The anti-inflammatory activity of the compounds of this invention may be assayed by measuring the ability of the compound to inhibit COX I and COX II, especially COX II, in vitro, using a radiometric assay, as described in more detail in Example 10. It may also be assayed by in vivo assays such as the Rat Carrageenan Paw and Rat Air-Pouch assays, as described in more detail in Examples 11 and 12 The analgesic activity of the compounds of this invention may be assayed by in vivo assays such as the Randall-Selitto assay and the rat arthritis pain model, as described in Example 13.

Administration and Pharmaceutical Composition

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula I may range from approximately 0.005–10 mg per kilogram body weight of the recipient per day; preferably about 0.05–1 mg/kg/day. Thus, for administration to a 70 kg person, the dosage range would preferably be about 3.5 mg to 400 mg per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen, which can be adjusted according to the degree of affliction. Compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semi-solid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol, and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in *Remington's Pharmaceutical Sciences*, edited by E. W. Martin (Mack Publishing Company, 18th ed., 1990).

The level of the compound in a formulation can vary within the full range employed by those skilled in the art. Typically, the formulation will contain, on a weight percent (wt %) basis, from about 0.01–99.99 wt % of a compound of Formula V based on the total formulation, with the balance being one or more suitable pharmaceutical excipients. Preferably, the compound is present at a level of about 1–80 wt %. Representative pharmaceutical formulations containing a compound of Formula I are described in Example 7.

EXAMPLES

The following preparations and examples are given to enable those skilled in the art to more clearly understand and to practice the present invention. They should not be considered as limiting the scope of the invention, but merely as being illustrative and representative thereof.

Example 1

3-(4-Fluoro-phenylsulfanyl)-6-methanesulfonyl-2-methyl-1H-indole

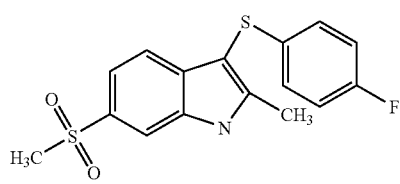

Step 1:

Preparation of 2-methyl-6-methylsulfanyl-indole-1-carboxylic acid tert-butyl ester 2-Methyl-6-methylthioindole (13.9 g) prepared according to Allais A. et al. *Eur. J. Med. Chem.—Chim. Ther.* (1975), 10(2), 187–99, was dissolved in $CH_3CN$ (150 mL) followed by the addition of $(BOC)_2O$ (18 g) with 480 mg DMAP. After 5 h the mixture was evaporated to dryness and the resulting 2-methyl-6-methylsulfanyl-indole-1-carboxylic acid tert-butyl ester was purified by chromatography over silica gel.

Step 2:

Preparation of 6-methanesulfonyl-2-methyl-1H-indole-1-carboxylic acid tert-butyl ester The product of step 1 (20.3 g) was treated with 135 g OXONE™ in 300 mL 1:1 MeOH/water for 2 h. The mixture was partitioned between methylene chloride and water, the organic layer was separated, washed, dried, and evaporated to dryness to yield 6-methanesulfonyl-2-methyl-indole-1-carboxylic acid tert-butyl ester (16 g) as a solid.

Step 3:

Preparation of 6-methanesulfonyl-2-methyl-1H-indole

The above product of step 2 was dissolved in 100 mL methylene chloride and treated with 12 mL TFA. After stirring overnight, the volatiles were removed and the product crystallized from 10:1 methylene chloride/MeOH. In this way 8.0 g of 6-methanesulfonyl-2-methyl-1H-indole was obtained.

Step 4:

Preparation of 3-(4-fluoro-phenylsulfanyl)-6-methanesulfonyl-2-methyl-1H-indole

A solution of 6-methanesulfonyl-2-methyl-1H-indole (207 mg, 1 mmol) in 6 mL of hexafluoroisopropanol was treated with 4-fluorothiophenol (2 mmol) followed by addition of PIFA (1.5 mmol). The dark colored solution was stirred for 30 minutes followed by partitioning between EtOAc and water. Purification by TLC (2:1 hexane/EtOAc) afforded 145 mg of 3-(4-fluoro-phenylsulfanyl)-6-methanesulfonyl-2-methyl-1H-indole, 101, MS: 336 ($[M+H]^+$).

Similarly, following the procedure described above in Step 4, but replacing 4-fluorothiophenol with the appropriately substituted thiophenol the additional compounds of Formula I wherein A is —S—, were prepared:

6-methanesulfonyl-3-(4-methoxy-phenylsulfanyl)-2-methyl-1H-indole, 102, MS: 348 ($[M+H]^+$);

3-(4-chloro-phenylsulfanyl)-6-methanesulfonyl-2-methyl-1H-indole, 103, MS: 353 ($[M+H]^+$);

3-(2,4-difluoro-phenylsulfanyl)-6-methanesulfonyl-2-methyl-1H-indole, 104, MS: 354 ($[M+H]^+$); and 3-(2-chloro-4-fluoro-phenylsulfanyl)-6-methanesulfonyl-2-methyl-1H-indole, 105, MS: 371 ($[M+H]^+$).

Oxidation of 3-(4-fluoro-phenylsulfanyl)-6-methanesulfonyl-2-methyl-1H-indole, 101 with one equivalent of Oxone™, yielded 3-(4-Fluoro-benzenesulfinyl)-6-methanesulfonyl-2-methyl-1H-indole 106, MS: 352 ($[M+H]^+$)

Example 2

3-(4-Bromo-benzyl)-6-methanesulfonyl-2-methyl-1H-indole

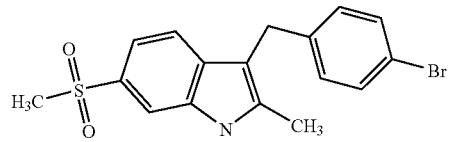

A solution of 6-methanesulfonyl-2-methyl-1H-indole (112 mg), prepared as described in Example 1 Step 3, in 9 ml $CH_2Cl_2$ was treated with p-bromo-benzaldehyde (100 mg) and 0.2 ml TMS-OTf. After cooling to 0° C., 0.26 ml of $Et_3SiH$ was added. The solution was stirred for 30 minutes followed by partitioning between EtOAc and water. Purification by TLC (2:1 hexane/EtOAc) gave 130 mg of 3-(4-bromo-benzyl)-6-methanesulfonyl-2-methyl-1H-indole 201, MS: 379 ($[M+H]^+$).

Similarly, following the procedure described above, but replacing p-bromobenzaldehyde with the appropriately substituted benzaldehyde, the additional compounds of Formula I wherein A is —C—, were prepared:

3-(4-Fluoro-benzyl)-6-methanesulfonyl-2-methyl-1H-indole 202, MS: 318 ($[M+H]^+$);

3-(3-Fluoro-benzyl)-6-methanesulfonyl-2-methyl-1H-indole 203, MS: 318 ($[M+H]^+$);

6-Methanesulfonyl-3-(4-methoxy-benzyl)-2-methyl-1H-indole 204, MS: 318 ($[M+H]^+$);

6-Methanesulfonyl-2-methyl-3-naphthalen-2-ylmethyl-1H-indole 205, MS: 350 ($[M+H]^+$);

6-Methanesulfonyl-2-methyl-3-(4-methyl-benzyl)-1H-indole 206, MS: 314 ([M+H]⁺);
6-Methanesulfonyl-2-methyl-3-(4-trifluoromethyl-benzyl)-1H-indole; 207, MS: 368 ([M+H]⁺);
3-(2,4-Difluoro-benzyl)-6-methanesulfonyl-2-methyl-1H-indole 208, MS: 336 ([M+H]⁺);
6-Methanesulfonyl-2-methyl-3-(4-methylsulfanyl-benzyl)-1H-indole 209, MS: 346 ([M+H]⁺);
6-Methanesulfonyl-3-(4-methoxy-naphthalen-1-ylmethyl)-2-methyl-1H-indole 210, MS: 380 ([M+H]⁺);
3-(2-Chloro-benzyl)-6-methanesulfonyl-2-methyl-1H-indole 211, MS: 335 ([M+H]⁺);
3-(4-Chloro-benzyl)-6-methanesulfonyl-2-methyl-1H-indole 212, MS: 335 ([M+H]⁺); and
6-Methanesulfonyl-2-methyl-3-(4-methylsulfonyl-benzyl)-1H-indole 213, MS: 378 ([M+H]⁺).

Example 3

3-(2,4-Difluoro-phenylsulfanyl)-6-methanesulfonyl-1H-indole-2-carbonitrile

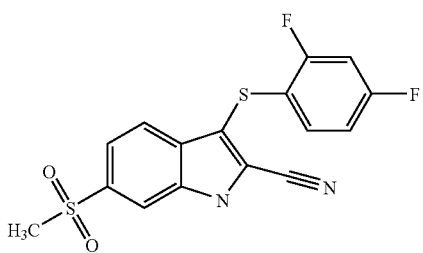

Step 1:

Preparation of 2-carbomethoxy-6-methylsulfonylindole

Sodium (16.6 g) was dissolved in 600 ml MeOH and cooled to −20° C. A mixture of methyl diazoacetate (83.2 g), 4-thiomethylbenzaldehyde, and 30 ml MeOH was added dropwise over 45 min. After stirring 3 h at −20° C. the mixture was kept at 0° C. in the refrigerator for two days. The material was partitioned between EtOAc and water to remove a large quantity of solid polymer. After drying and solvent removal the crude azidoester was dissolved in 700 ml toluene and refluxed for 3 h. The solvent was removed and the resulting 2-carbomethoxy-6-methylthioindole was purified by flash chromatography. The product was then dissolved in 200 ml MeOH and 100 ml THF. OXONE™ (3 eq) in 100 ml water was added and the reaction was stirred for 2 h at room temperature. The mixture was partitioned between CH₂Cl₂ and water. The product, 2-carbomethoxy-6-methylsulfonylindole, was obtained as a white solid upon evaporation of the organic phase (16.0 g).

Step 2:

Preparation of 3-(2,4-difluoro-phenylsulfanyl)-6-methanesulfonyl-1H-indole-2-carboxylic acid methyl ester A solution of 2-carbomethoxy-6-methylsulfonylindole (750 mg, 2.8 mmol), in 10 mL hexafluoroisopropanol was treated with 2,4-difluorothiophenol (7.5 mmol) followed by addition of PIFA (5.6 mmol). The dark colored solution was stirred overnight then partitioned between methylene chloride and water. After concentration of the methylene chloride layer to 20 mL the product was precipitated by addition of 30 mL hexane. An 88% yield of 3-(2,4-difluoro-phenylsulfanyl)-6-methanesulfonyl-1H-indole-2-carboxylic acid methyl ester was obtained.

Step 3:

Preparation of 3-(2,4-difluoro-phenylsulfanyl)-6-methanesulfonyl-1H-indole-2-carboxylic acid amide The product from step 2 was stirred for 36 h with 4.5 eq LiOH in 12 mL 1:1 water/THF. The mixture was partitioned between EtOAc and 2N HCl to obtain the crude acid. This material (452 mg) was dissolved in 8 mL benzene and 3 mL methylene chloride, and treated with 0.16 mL oxalyl chloride and a catalytic amount of DMF. After stirring 14 h, 10 mL 0.5M NH₃ in dioxane was added. After stirring 3 h the mixture was partitioned between water and methylene chloride. The product was purified by TLC (5% MeOH/methylene chloride). The yield of 3-(2,4-difluoro-phenylsulfanyl)-6-methanesulfonyl-1H-indole-2-carboxylic acid amide was 427 mg.

Step 4:

Preparation of the 3-(2,4-difluoro-phenylsulfanyl)-6-methanesulfonyl-1H-indole-2-carbonitrile The amide, of step 3, (250 mg) was dissolved in 8 mL dioxane and treated with TFA-anhydride (0.28 mL) and pyridine (0.4 mL). After 6 h the reaction was concentrated and purified by TLC (3% MeOH/methylene chloride). The 3-(2,4-difluoro-phenylsulfanyl)-6-methanesulfonyl-1H-indole-2-carbonitrile 301 (220 mg) was obtained as a solid, MS: 365 ([M+H]⁺).

Similarly, following the procedure described above in step 2, but replacing 2,4-difluorothiophenol with the appropriate substituted thiophenol the additional compounds of Formula I wherein A is —S—, were prepared:

3-(4-Fluoro-phenylsulfanyl)-6-methanesulfonyl-1H-indole-2-carbonitrile, 302, MS: 347 ([M+H]⁺);
6-Methanesulfonyl-3-p-tolylsulfanyl-1H-indole-2-carbonitrile, 303, MS: 343 ([M+H]⁺);
6-Methanesulfonyl-3-(4-methoxy-phenylsulfanyl)-1H-indole-2-carbonitrile, 304, MS: 365 ([M+H]⁺);
3-(2-Chloro-phenylsulfanyl)-6-methanesulfonyl-1H-indole-2-carbonitrile, 305, MS: 364 ([M+H]⁺);
3-(2-Chloro-4-methoxy-phenylsulfanyl)-6-methanesulfonyl-1H-indole-2-carbonitrile, 306, MS: 394 ([M+H]⁺);
3-(4-Chloro-phenylsulfanyl)-6-methanesulfonyl-1H-indole-2-carbonitrile, 307, MS: 364 ([M+H]⁺);
3-(2-Fluoro-4-methoxy-phenylsulfanyl)-6-methanesulfonyl-1H-indole-2-carbonitrile, 308, MS: 377 ([M+H]⁺);
3-(2,4-Difluoro-benzenesulfinyl)-6-methanesulfonyl-1H-indole-2-carbonitrile, 309, MS: 381 ([M+H]⁺);
6-Methanesulfonyl-3-(4-ethoxy-benzyl)-1H-indole-2-carbonitrile, 311, MS: 373 ([M+H]⁺)

Similarly, following the procedure described above in Step 2, but replacing 2,4-difluorothiophenol with the appropriate substituted thiophenol, and omitting Step 4 the additional compounds of Formula I wherein A is —S—, were prepared:

3-(2-Chloro-4-methoxy-phenylsulfanyl)-6-methanesulfonyl-1H-indole-2-carboxylic acid amide, 315, MS: 412 ([M+H]⁺);
3-(2-Chloro-phenylsulfanyl)-6-methanesulfonyl-1H-indole-2-carboxylic acid amide, 316, MS: 382 ([M+H]⁺);

6-Methanesulfonyl-3-(4-methoxy-phenylsulfanyl)-1H-indole-2-carboxylic acid amide, 317, MS: 377 ([M+H]⁺);
3-(2,4-Difluoro-phenylsulfanyl)-6-methanesulfonyl-1H-indole-2-carboxylic acid amide, 318, MS: 383 ([M+H]⁺);
3-(4-Fluoro-phenylsulfanyl)-6-methanesulfonyl-1H-indole-2-carboxylic acid amide, 319, MS: 382 ([M+H]⁺); and
6-Methanesulfonyl-3-p-tolylsulfanyl-1H-indole-2-carboxylic acid amide, 320, MS: 382 ([M+H]⁺).

Similarly, following the procedure described above in Step 2, but replacing 2,4-difluorothiophenol with the appropriate substituted thiophenol followed by alkylation of the amide obtained in Step 3 by methods known to those skilled in the art, the additional compounds of Formula I wherein A is —S—, were prepared:

3-(2,4-Difluoro-phenylsulfanyl)-6-methanesulfonyl-1H-indole-2-carboxylic acid butylamide, 321, MS: 439 ([M+H]⁺);
3-(2,4-Difluoro-phenylsulfanyl)-6-methanesulfonyl-1H-indole-2-carboxylic acid isopropylamide, 322, MS: 425 ([M+H]⁺);
3-(2,4-Difluoro-phenylsulfanyl)-6-methanesulfonyl-1H-indole-2-carboxylic acid dimethylamide, 323, MS: 411 ([M+H]⁺);
3-(2,4-Difluoro-phenylsulfanyl)-6-methanesulfonyl-1H-indole-2-carboxylic acid diethylamide, 324, MS: 439 ([M+H]⁺);
3-(2,4-Difluoro-phenylsulfanyl)-6-methanesulfonyl-1H-indole-2-carboxylic acid propylamide, 325, MS: 425 ([M+H]⁺);
3-(2,4-Difluoro-phenylsulfanyl)-6-methanesulfonyl-1H-indole-2-carboxylic acid methylamide, 326, MS: 397 ([M+H]⁺);
3-(2,4-Difluoro-phenylsulfanyl)-6-methanesulfonyl-1H-indole-2-carboxylic acid ethylamide, 327, MS: 411 ([M+H]⁺);
3-(2-Fluoro-phenylsulfanyl)-6-methanesulfonyl-1H-indole-2-carboxylic acid isopropylamide, 328, MS: 366 ([M+H]⁺);
3-(2-Fluoro-phenylsulfanyl)-6-methanesulfonyl-1H-indole-2-carboxylic acid butylamide, 329, MS: 420 ([M+H]⁺);
3-(2-Fluoro-phenylsulfanyl)-6-methanesulfonyl-1H-indole-2-carboxylic acid ethylamide, 330, MS: 393 ([M+H]⁺);
3-(2-Fluoro-phenylsulfanyl)-6-methanesulfonyl-1H-indole-2-carboxylic acid propylamide, 331, MS: 407 ([M+H]⁺);
3-(2-Chloro-phenylsulfanyl)-6-methanesulfonyl-1H-indole-2-carboxylic acid isopropylamide, 332, MS: 407 ([M+H]⁺);
3-(2-Chloro-phenylsulfanyl)-6-methanesulfonyl-1H-indole-2-carboxylic acid butylamide, 333, MS: 438 ([M+H]⁺);
3-(2-Chloro-phenylsulfanyl)-6-methanesulfonyl-1H-indole-2-carboxylic acid ethylamide, 334, MS: 410 ([M+H]⁺);
3-(2-Chloro-phenylsulfanyl)-6-methanesulfonyl-1H-indole-2-carboxylic acid diethylamide, 335, MS: 438 ([M+H]⁺);
3-(2-Fluoro-phenylsulfanyl)-6-methanesulfonyl-1H-indole-2-carboxylic acid methylamide, 336, MS: 379 ([M+H]⁺);
3-(2-Fluoro-phenylsulfanyl)-6-methanesulfonyl-1H-indole-2-carboxylic acid dimethylamide, 337, MS: 393 ([M+H]⁺); and
3-(2-Fluoro-phenylsulfanyl)-6-methanesulfonyl-1H-indole-2-carboxylic acid diethylamide, 338, MS: 421 ([M+H]⁺).

Example 4

3-(4-Fluoro-phenoxy)-6-methanesulfonyl-2-methyl-1H-indole

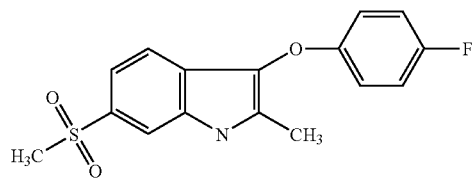

Step 1:

Preparation of 1-(4-fluoro-phenoxy)-propan-2-one

To a mixture of para-fluorophenol (15 g) and K₂CO₃ (18.5 g) in 100 mL acetone were added chloroacetone (10.4 mL) and of KI (22 g). After heating at reflux for 18 h the reaction mixture was cooled down and left at RT overnight. The reaction mixture was filtered, washed with acetone, and evaporated to dryness. The residue was partitioned between dichloromethane and water, the organic layer was separated and washed with water, dried over MgSO₄, and evaporated to yield 15 g of 1-(4-fluoro-phenoxy)-propan-2-one as a yellow liquid.

Step 2:

Preparation of (3-methanesulfonyl-phenyl)-hydrazine

To a solution of 3-methanesulphonyl-phenylamine (2.5 g) in 6 mL HCl was added a solution of NaNO₂ in 5 mL of H₂O at −5° to 0° C. After stirring for 30 min the resulted diazonium salt was poured into a cold solution (−10° to −15° C.) of stannous chloride in 6 ml HCl. The mixture of resulted hydrazine hydrochloride in HCl was stored in the refrigerator overnight. The solution was basified to pH 10, by addition of a 6N solution of NaOH, and extracted with THF. The organic layer was washed, dried over MgSO₄, and evaporated to yield 2 g of a light brown solid (3-methanesulfonyl-phenyl)-hydrazine.

Step 3:

3-(4-Fluoro-phenoxy)-6-methanesulfonyl-2-methyl-1H-indole

To the solution of (3-methanesulfonyl-phenyl)-hydrazine (1.35 g) and 1-(4-fluoro-phenoxy)-propan-2-one (1.01 g) in benzene at RT was added equimolar amount of PCl₃. The reaction mixture was stirred at RT for 1 hour and the solvent was removed in vacuo. The residue was purified by Biotage chromatography, eluted with 10–30% EtOAc/Hexane to yield 0.1 g of 3-(4-fluoro-phenoxy)-6-methanesulfonyl-2-methyl-1H-indole 401 as a light orange powder, MS: 320 ([M+H]⁺).

Similarly, following the procedure in Step 3 described above, but replacing 1-(4-fluoro-phenoxy)-propan-2-one with the appropriately substituted phenoxy-propane-2-one the additional compounds of Formula I wherein A is —O— were prepared:

3-(2-Chloro-4-methoxy-phenoxy)-6-methanesulfonyl-2-methyl-1H-indole, 402, MS: 366 ([M+H]⁺);
3-(2,4-Difluoro-phenoxy)-6-methanesulfonyl-2-methyl-1H-indole, 403, MS: 377 ([M+H]⁺);
3-(2,4-Dichloro-phenoxy)-6-methanesulfonyl-2-methyl-1H-indole 404, MS: 370 ([M+H]⁺);

3-(4-Chloro-phenoxy)-6-methanesulfonyl-2-methyl-1H-indole 405, MS: 336 ([M+H]⁺).

Example 5

(6-Methanesulfonyl-3-phenylsulfanyl-1H-indol-2-yl)-methanol

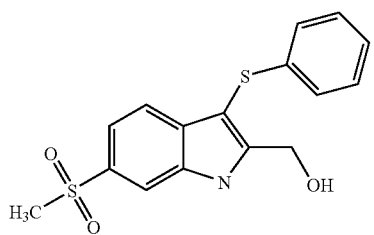

A solution of (6-methanesulfonyl-3-phenylsulfanyl-1H-indol-2-yl)-2-carboxylic acid methyl ester (800 mg), prepared as in Example 3, Steps 1 and 2, in THF (35 mL) was treated with 5.6 mL 1.5M DIBAL in toluene at −78° C. then allowed to warm to room temperature over 30 minutes. It was poured into 3N HCl and extracted with EtOAc. The product was purified by SiO₂ chromatography (eluting with 30% EtOAc/hexane) to yield 686 mg of (6-methanesulfonyl-3-phenylsulfanyl-1H-indol-2-yl)-methanol 501, MS: 334 ([M+H]⁺).

Similarly, following the procedure described above [3-(4-Fluoro-phenylsulfanyl)-6-methanesulfonyl-1H-indol-2-yl]-methanol 502, MS: 352 ([M+H]⁺) was prepared.

Example 6

3-(2-Chloro-phenylsulfanyl)-6-methanesulfonyl-2-methanesulfonylmethyl-1H-indole

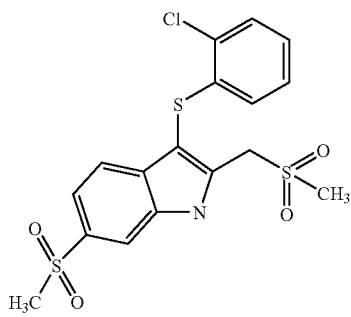

[3-(2-chloro-phenylsulfanyl)-6-methanesulfonyl-1H-indol-2-yl]-methanol (1 mmole) (as prepared in Example 5) was dissolved in 2 mL CH₂Cl₂ and treated with 0.3 mL NEt₃ followed by 0.08 ml MsCl. After stirring 10 min. 3 mL DMF was added followed by 0.5 g NaSO₂Me. The mixture was stirred overnight. The reaction mixture was evaporated to dryness and applied to a PTLC plate. Elution with 1:1 EtOAc/hexane gave 80 mg 3-(2-chloro-phenylsulfanyl)-6-methanesulfonyl-2-methanesulfonylmethyl-1H-indole 601, MS: 343 ([M+H]⁺).

Example 7

Acetic acid 3-(2-chloro-phenylsulfanyl)-6-methanesulfonyl-1H-indol-2-yl methyl ester

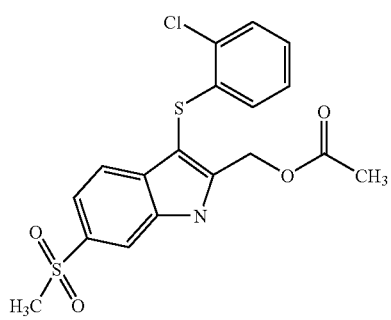

A solution of [3-(2-chloro-phenylsulfanyl)-6-methanesulfonyl-1H-indol-2-yl]-methanol (75 mg) (prepared as described in example 5) in pyridine (2 mL) was treated with 0.5 mL Ac₂O. After 30 min. all volatiles were removed to yield 82 mg of acetic acid 3-(2-chloro-phenylsulfanyl)-6-methanesulfonyl-1H-indol-2-yl methyl ester 701, MS: 411 ([M+H]⁺).

Example 8

3-(2-Chloro-phenylsulfanyl)-6-methanesulfonyl-1H-indole-2-carbaldehyde

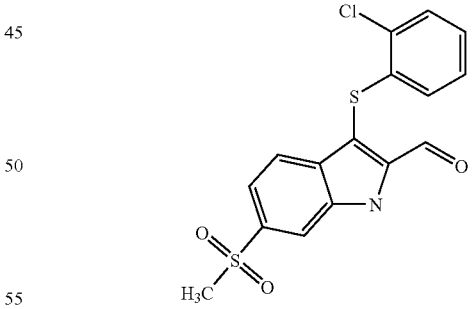

A solution of alcohol [3-(2-chloro-phenylsulfanyl)-6-methanesulfonyl-1H-indol-2-yl]-methanol (75 mg) (prepared as described in Example 5) in CH₂Cl₂ (5 ml) was added to a solution of DMSO (0.2 ml) and oxalyl chloride (0.1 ml) that had been prepared at −78°. After 15 min triethylamine (0.45 ml) was added and the reaction was allowed to warm to 20° over 30 min. It was partitioned between EtOAc and water and the organic phase evaporated to give 3-(2-chloro-phenylsulfanyl)-6-methanesulfonyl-1H-indole-2-carboxaldehyde, 801, MS: 343 ([M+H]⁺).

Example 9

The following are representative pharmaceutical formulations containing a compound of Formula I.

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| crosscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Injectable Formulation

The following ingredients are mixed to form an injectable formulation.

| Ingredient | Amount |
| --- | --- |
| compound of this invention | 0.4 mg |
| sodium acetate buffer solution, 0.4 M | 2.0 mL |
| HCl (1 N) or NaOH (1 N) | q.s. to suitable pH |
| water (distilled, sterile) | q.s. to 20 mL |

Example 10

Inhibition of COX I and COX II In Vitro

The COX I and COX II inhibitory activity of compounds of this invention in vitro was determined using partially purified COX I and COX II enzymes, prepared as described in J. Barnett et al., *Biochim. Biophys. Acta*, 1209, 130–139 (1994).

COX I and COX II samples were diluted with Tris-HCl buffer (50 mM Tris-HCl, pH 7.9) containing 2 mM EDTA and 10% glycerol and reconstituted by incubating first with 2 mM phenol for 5 minutes and then with 1 micromolar hematin for an additional 5 minutes. 125 µl of the reconstituted COX I or COX II enzyme were pre-incubated for 10 minutes at room temperature in a shaking water bath with the compounds of the invention dissolved in 2–15 µl of DMSO or the carrier vehicles (control samples). The enzyme reaction was initiated by adding 25 µl of 1-[14 C] arachidonic acid (80,000–100,000 cpm/tube; 20 micromolar final concentration) and the reaction was allowed to continue for an additional 45 seconds. The reaction was terminated by adding 100 µl of 2N HCl and 750 µl water. An aliquot (950 µl) of the reaction mixture was loaded onto a 1 mL $C_{18}$ Sep-Pak column (J. T. Baker, Phillipsburg, N.J.) which had been previously washed with 2–3 mL methanol and equilibrated with 5–6 mL distilled water. Oxygenated products were quantitatively eluted with 3 mL of acetonitrile/water/acetic acid (50:50:0.1, v/v) and the radioactivity in the eluate determined in a scintillation counter. Compounds of this invention were active in this assay for COX II.

Example 11

Anti-inflammatory Activity

The anti-inflammatory activity of compounds of this invention was determined by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" *Proc. Soc. Exp. Biol. Med*. 111, 544–547, (1962). This assay has been used as a primary in vivo screen for anti-inflammatory activity of most NSAIDs, and is considered predictive of human efficacy. Briefly, test materials were administered orally to female rats in a volume of 1 mL prepared as solutions or suspensions in an aqueous vehicle containing 0.9% sodium chloride, 0.5% sodium carboxymethyl-cellulose, 0.4% polysorbate 80, 0.9% benzyl alcohol, and 97.3% distilled water. Control rats received vehicle alone. After 1 h 0.05 mL of a 0.5% solution of Carrageenan (Type IV Lambda, Sigma Chemical Co.) in 0.9% saline was injected into the subplantar region of the right hind paw. Three hours later the rats were euthanized in a carbon dioxide atmosphere; hind paws were removed by severing at the tatso-crural joint; and the left and right paws were weighed. The increase in weight of the right paw over the left paw was obtained for each animal and the mean increases were calculated for each group. The anti-inflammatory activity of the test materials is expressed as the percent inhibition of the increase in hind paw weight of the test group relative to the vehicle dosed control group.

Compounds of this invention were active in this assay.

Example 12

Inhibition of Eicosanoid Synthesis In Vivo

The activity of compounds of this invention in inhibiting in vivo eicosanoid (prostaglandin $E_2$) synthesis in inflamed tissues was determined by the carrageenan-induced inflammation (air-pouch model) in rats, using a modification of the method described in Futaki, M., et al., "Selective Inhibition of NS-398 on prostanoid production in inflamed tissue in rat Carrageenan Air-pouch Inflammation" *J. Pharm. Pharmacol.* 45, 753–755, (1993) and Masferrer, J. L., et al.; "Selective Inhibition of inducible cyclooxygenase 2 in vivo is Antiflammatory and Nonulcerogenic" *Proc. Natl. Acad. Sci. USA*. 91, 3228–3232, (1994). In this assay, an air-pouch is created in the rat and the $PGE_2$ levels in the air-pouch exudate are measured by enzyme immunoassay. Briefly, male rats were anesthetized using a 60:40 $CO_2:O_2$ mixture and subsequently injected subcutaneously with 20 mL of sterilized air, under aseptic conditions, in the proximal area of the dorsum. This injection of sterile air causes the creation of a subcutaneous "air pouch". The next day, a further 10 mL of sterile air was injected into the previously formed pouch using the same technique. The test materials were administered orally in a volume of 1 mL/100 g body weight as solutions or suspensions in an aqueous vehicle containing 0.9% sodium chloride, 0.5% sodium carboxymethyl-cellulose, 0.4% polysorbate 80, 0.9% benzyl alcohol, and 97.3% water. Control rats received vehicle alone. After 30 minutes, 5 mL of a 0.5% solution of carrageenan (Sigma, Lambda Type IV) was injected into the air pouch. The rats were euthanized 3 or 6 h after the compound administration. 10 mL of a solution containing 10 µg/l of indomethacin and 5.4 mM EDTA in 0.9% sterile saline was injected into the air pouch; the air pouch was cut open; and the exudate was harvested. The total exudate volume was recorded, and the samples were analyzed for $PGE_2$ and 6-keto PGF, by ELISA (Titerzyme®, PerSeptive Diagnostics, Boston, Mass.) and $TxB_2$ by radioimmuno assay (New England Nuclear Research, Boston Mass., Catalog No. NEK-037), according to the manufacturer's directions.

The mean concentrations of $PGE_2$ were calculated for each group. The anti-inflammatory activity of test materials is expressed as the percent inhibition of $PGE_2$ formation in the test group relative to the control group.

Compounds of this invention were active in this assay.

Example 13

Analgesic Activity

The analgesic activity of the compounds of this invention may be determined by using a modification of the method described in Randall, L. O., and Selitto, J. J., "A Method for Measurement of Analgesic Activity on Inflamed Tissue", *Arch. Int. Pharmacodyn.*, CXI, 4, 409, (1957) and Gans, et. al., "Anti-Inflammatory and Safety Profile of DuP 697, a Novel Orally Effective Prostaglandin Synthesis Inhibitor", *J. Pharmcol. Exp. Ther.*, 254, No. 1,180, (1990). In this assay, the male Sprague Dawley rats were injected with 0.1 mL of 20% brewer's yeast in deionized water (Sigma, St. Louis) in the subplantar region of the left hind foot. After 2 h, the test materials were administered orally in a volume of 1 mL/100 g body weight as solutions or suspensions in an aqueous vehicle containing 0.9% sodium chloride, 0.5% sodium carboxymethyl-cellulose, 0.4% polysorbate 80, 0.9% benzyl alcohol, and 97.3% water. Control rats received vehicle alone. After 1 h, the hindpaw was placed on the platform of a Basile Analgesy-Meter (Ugo Biological Research Apparatus, Italy, Model # 7200) and mechanical force was applied to the dorsum of the rat's hindpaw. Compounds of the invention were active in this assay.

The analgesic activity of compounds of this invention may also be determined by using an adjuvant-induced arthritis pain model in the rat, where pain is assessed by the animal's vocal response to the squeezing or flexing of an inflamed ankle joint, as described in Winter C. A. and Nuss, G. W., "Treatment of Adjuvant Arthritis in rats with Anti-inflammatory Drugs", *Arthritis Rheum.*, 9, 394–403, (1966) and Winter, C. A., Kling P. J., Tocco, D. J., and Tanabe, K., "Analgesic activity of Diflunisal [MK-647; 5-(2,4-Difluorophenyl)salicylic acid] in Rats with Hyperalgesia Induced by Freund's Adjuvant", *J. Pharmacol. Exp. Ther.*, 211, 678–685, (1979).

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

What is claimed is:

1. A process for preparing a compound, which comprises: reacting a compound of general Formula

wherein
R² is hydrogen alkyl, alkoxy hydroxy, halo, haloalkyl, nitro, cyano, or —NR⁵R⁶, wherein R⁵ and R⁶ are each independently hydrogen or alkyl; and
R is lower alkyl,
with a compound of general Formula ArAH, to provide a compound of Formula (I):

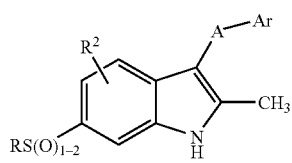

wherein A is —S—,

Ar is an optionally substituted phenyl, and

R is lower alkyl.

2. The method of claim 1, wherein R is methyl.

3. The method of claim 2, wherein Ar is 4-fluorophenyl.

4. The method of claim 2, wherein Ar is 4-bromophenyl.

5. The method of claim 2, wherein Ar is 2,4-difluorophenyl.

6. The method of claim 2, wherein Ar is 2-chlorophenyl.

* * * * *